(12) United States Patent
Lariviere et al.

(10) Patent No.: US 12,400,560 B2
(45) Date of Patent: Aug. 26, 2025

(54) TRAINING STATION FOR SURGICAL PROCEDURES

(71) Applicants: Anne Marie Lariviere, Bogotá (CO); Paulo Andrés Escobar Rincón, Bogotá (CO)

(72) Inventors: Anne Marie Lariviere, Bogotá (CO); Paulo Andrés Escobar Rincón, Bogotá (CO)

( * ) Notice: Subject to any disclaimer, the term of this patent is extended or adjusted under 35 U.S.C. 154(b) by 19 days.

(21) Appl. No.: 18/414,689

(22) Filed: Jan. 17, 2024

(65) Prior Publication Data

US 2024/0153408 A1    May 9, 2024

Related U.S. Application Data

(63) Continuation of application No. PCT/IB2022/056814, filed on Jul. 22, 2022.

(30) Foreign Application Priority Data

Jul. 30, 2021    (CO) .......................... NC2021/0010157

(51) Int. Cl.
    *G09B 23/30*     (2006.01)
    *A61B 34/10*     (2016.01)
    *A61B 90/00*     (2016.01)

(52) U.S. Cl.
    CPC .............. *G09B 23/30* (2013.01); *A61B 34/10* (2016.02); *A61B 90/37* (2016.02);
    (Continued)

(58) Field of Classification Search
    CPC ...... G09B 23/28; G09B 23/30; G09B 23/306; G09B 23/32; G09B 23/34
    See application file for complete search history.

(56) References Cited

U.S. PATENT DOCUMENTS

| | | |
|---|---|---|
| 6,908,309 B2 | 6/2005 | Gil et al. |
| 10,181,270 B1 | 1/2019 | Fuller |
| | (Continued) | |

FOREIGN PATENT DOCUMENTS

| | | |
|---|---|---|
| AU | 2013323255 B2 | 2/2018 |
| CN | 207704729 U | 8/2018 |
| | (Continued) | |

OTHER PUBLICATIONS

Rancati, Alberto; Moina, Daniel; Moina, Gabriel; Dorr, Julio; Ripetta, Julio; Horgon, Santiago. (2014) Rhinotrainer, Surgical Nose Simulator. Surgery: Current Research. 04. 10.4172/2161-1076. 1000205.

(Continued)

*Primary Examiner* — Kang Hu
*Assistant Examiner* — Correll T French
(74) *Attorney, Agent, or Firm* — The Morales Law Firm; Joseph L. Morales, Esq.

(57) ABSTRACT

The present invention refers to a training station for surgical procedures comprising a model of an anatomical structure, a three-dimensional digital model of the anatomical structure and a work base. The model of the anatomical structure is obtained through diagnostic images of a patient and provides a replica of the anatomical conformation including bone, cartilage and skin. The three-dimensional digital model allows a training station user to interact with a virtual representation of the model of an anatomical structure through augmented reality and/or virtual reality systems.

8 Claims, 15 Drawing Sheets

(52) U.S. Cl.
CPC ... *A61B 2034/105* (2016.02); *A61B 2090/365* (2016.02); *A61B 2090/3762* (2016.02)

(56) References Cited

U.S. PATENT DOCUMENTS

| | | |
|---|---|---|
| 2007/0020598 A1 | 1/2007 | Yamashita et al. |
| 2012/0034587 A1* | 2/2012 | Toly .................. G09B 23/30 434/267 |
| 2014/0051049 A1* | 2/2014 | Jarc .................. G09B 23/30 434/267 |
| 2018/0174491 A1* | 6/2018 | Sauer ................. G09B 9/00 |
| 2021/0059755 A1 | 3/2021 | Villain et al. |
| 2021/0233429 A1* | 7/2021 | Barber ............... G09B 23/285 |
| 2022/0093009 A1* | 3/2022 | Lebovic ............. G09B 23/34 |

FOREIGN PATENT DOCUMENTS

| | | |
|---|---|---|
| CN | 111839728 A | 10/2020 |
| JP | 2016180962 A | 7/2016 |
| KR | 101693808 B1 | 1/2017 |
| RU | 182502 U1 | 8/2018 |

OTHER PUBLICATIONS

Zabaneh G, Lederer R, Grosvenor A, Wilkes G. Rhinoplasty: a hands-on training module. Plast Reconstr Surg. Sep. 2009;124(3):952-954. doi: 10.1097/PRS.0b013e3181b17bf5. PMID: 19730317.

Ho M, Goldfarb J, Moayer R, Nwagu U, Ganti R, Krein H, Heffelfinger R, Hutchinson ML. Design and Printing of a Low-Cost 3D-Printed Nasal Osteotomy Training Model: Development and Feasibility Study. JMIR Med Educ. Nov. 17, 2020;6(2):e19792. doi: 10.2196/19792. PMID: 33200998; PMCID: PMC7708083.

* cited by examiner

TRAINING STATION FOR SURGICAL PROCEDURES

TECHNICAL FIELD

The present invention refers to models of human organs and tissues, anatomical models and training models for surgical procedures in the field of medicine. More specifically, the present invention provides a replica of the anatomy of a real patient for cosmetic or corrective surgery training. It is also related to a three-dimensional digital model of the physical model with which the user can interact through augmented reality and/or virtual reality before, during or after training on the physical model.

BACKGROUND OF THE INVENTION

Surgeons conventionally require a large number of hours of training and practice to adequately master the techniques of their medical profession, thereby obtaining optimal results in said procedures. In general, training in any type of surgery is carried out on real patients with the support of experts in each type of intervention on cadavers, or, failing that, in training stations designed to simulate soft tissues, cartilage, bones and the particular defects of the procedure.

In general, the most appropriate training method is performed on cadavers, since it can provide an extensive understanding of the real implications that surgery could have on a patient, as well as the sensations needed to adjust the force applied to each type of tissue, the depth of the incisions, among others. However, adequate cadavers are rarely available for such training sessions, either due to the specific anatomical conditions required for each type of practice, due to the difficulty of obtaining the consents required for such procedures, or due to necessary logistical preservation requirements.

Interventions in real patients assisted by experts have the disadvantage of being potentially dangerous for patients, because a person with little training can seriously affect sensitive structures and bring about additional complications.

One of the most appropriate, economical and easily accessible methods for surgical training is through models that simulate the real structures that will be operated on. However, the models currently on the market do not achieve a sufficiently faithful reproduction of the specific structures, as well as the textures, consistencies and hardness of real organs. An example may be the difficulty of reproducing the human nasal anatomy, which contains bones, cartilage, fat and skin in specific areas and with thicknesses and structures that are difficult to replicate.

Likewise, it is known that interventions in this area to correct nasal obstructions, cosmetic deformities or trauma are highly complex, because the surgery is performed in a reduced area and requires delicate handling of the tissues; therefore, movements must be efficient and smooth enough to avoid damage.

Therefore, there is an important need for models that simulate in a sufficiently faithful and anatomically correct manner different structures of living beings, so as to facilitate adequate training for surgeons prior to an intervention in real patients.

BRIEF DESCRIPTION OF THE INVENTION

The present invention refers to models of human organs and tissues, anatomical models and training models for surgical procedures in the field of medicine. Particularly, the present invention provides a replica of an anatomically equivalent structure of a region of the anatomy of a real patient, including bone, cartilaginous structure, and soft tissues such as muscle, skin and fat. In order to obtain a replica that is as faithful as possible to the real organs, a careful selection of the materials of each of the replicated structures must be made, in to order provide sensations of texture, hardness and flexibility equivalent to those of the real structures.

The models according to the present invention use information acquired from diagnostic images of a real patient, performing a segmentation and three-dimensional reconstruction of each of the structures of interest in the most precise way possible, in order to provide the thicknesses, densities, sizes and specific positions of each of them.

In one embodiment of the invention, once the three-dimensional reconstructions have been obtained through diagnostic images, it is possible not only to obtain the physical model that will be used in training but also to use the three-dimensional digital model, which can be used to complement the training, since it allows the user to interact with a virtual representation through augmented reality and/or virtual reality technology.

According to one embodiment of the invention, the training station for surgical procedures is made up of a model of a particular anatomical structure of a patient, a three-dimensional digital model of the anatomical structure, and a work base. Preferably, the model of the anatomical structure corresponds to an equivalent anatomical conformation of a real patient, and is made up of materials that simulate bones, cartilage and soft tissues.

In some embodiments, the bone structure manages to faithfully replicate the properties of compression, tensile strength, flexion, elasticity, plasticity, rigidity, flexibility, resistance, among others, of a real bone. This bone structure can be obtained through appropriate 3D printing technologies.

In one embodiment of the invention, the required cartilaginous structures can also be obtained by 3D printing using the information obtained from the diagnostic images, to then be attached to the bone structure, forming an osteocartilaginous skeleton. As noted above, the selection of the materials is of great importance in order to obtain a result that accurately simulates the replicated area.

According to some embodiments of the invention, additional layers on the osteocartilaginous skeleton such as muscle, skin and fat can be included by means of molds designed to give the specific shapes and thicknesses of each of said layers, which can be adhered directly, or fused together, in order to obtain an adequate coupling of all the components of the model of the anatomical structure.

DETAILED DESCRIPTION OF THE INVENTION

Below, some embodiments of the training station of the invention are described, which refer to the figures that accompany the description. The training station for surgical procedures according to the present invention may include a model of a desired anatomical structure modeled from the particular anatomy of a real patient. The anatomical structure used in the training station is not particularly limited, and could correspond to any area of the desired anatomy. In particular, the selection of areas of the head and neck such as the pinna, temporal bone, lower and upper maxilla, or the nasal structure, among others, is preferred.

The particular features of the training station for surgical procedures according to the present invention are included in detail, using as example a model of a nasal structure.

Figure 1:
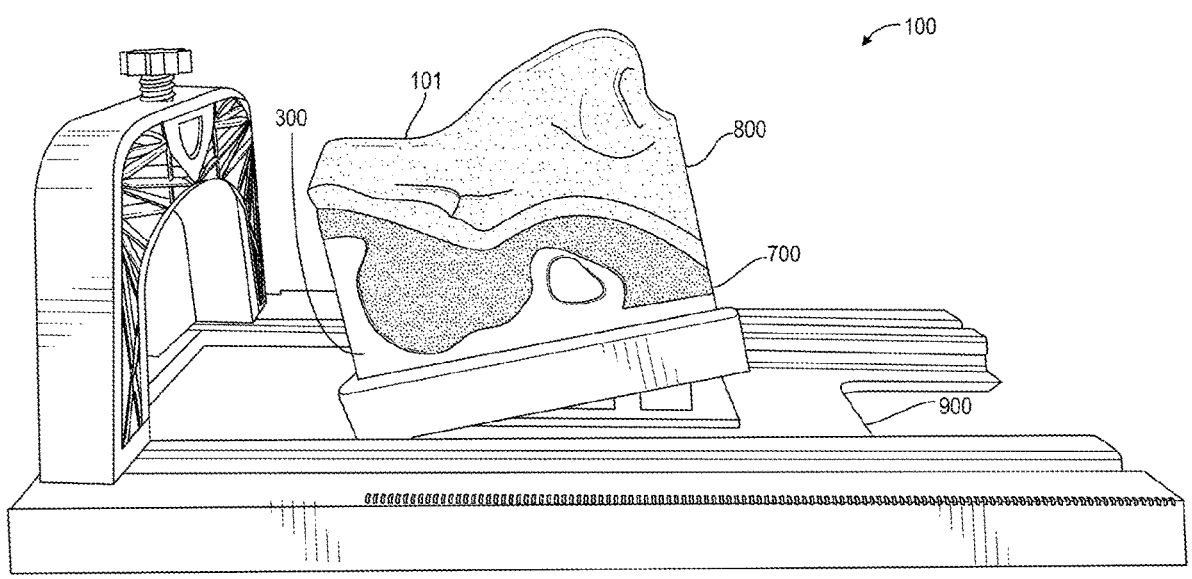
FIG. 1 corresponds to the training station for surgical procedures according to a preferred embodiment of the present invention.
Figure 2:
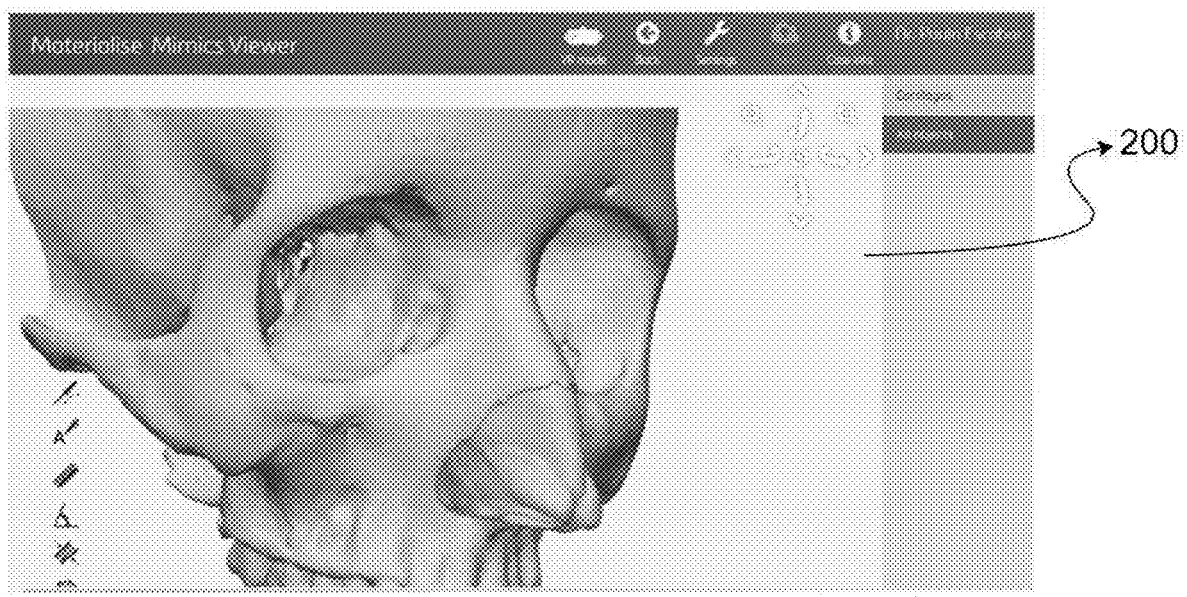
FIG. 2 is an illustrative image of the three-dimensional digital model of the nasal structure included in the training station according to an embodiment of the invention.

As illustrated in FIGS. 1 and 2, the invention provides a training station for surgical procedures (100) comprising: a model of an anatomical structure (101), a three-dimensional digital model (200) of the model of an anatomical structure (101), and a work base (900). Preferably, the model of the anatomical structure (101) corresponds to an equivalent anatomical conformation of a patient, and is made up of materials that simulate bones, cartilage and skin. The three-dimensional digital model (200) allows a training station user to interact with a representation of the model of an anatomical structure (101) through augmented reality and/or virtual reality systems. Likewise, the work base (900) has means for fixing it to the surface on which the training is carried out, and also has means for modifying the angle of the model during training.

According to some embodiments of the invention, the training station for surgical procedures (100) comprises a model of an anatomical structure (101) that may correspond, for example, to a nasal structure, composed of a faithful replica of said section from a real patient with features of interest for the practice of surgical procedures of the nose, both functional and aesthetic, such as septoplasty, turbinoplasty, surgery of the nasal dorsum, surgery of the nasal tip, surgery of the nasal base, of nasal flap surgery and/or non-surgical nose procedures, among others. The features of interest are selected, for example, from septal deviation, nasal hump, nasal tip deformity, among others.

The model of the anatomical structure (101) is obtained using information from diagnostic images acquired through techniques such as computed tomography, in which a volumetric helical acquisition is carried out in multidetector equipment, obtaining high resolution slices in axial, sagittal and coronal planes from the base of the skull in bone and soft tissue reconstruction algorithms. Diagnostic images can be complemented in special cases with images obtained from additional techniques such as magnetic resonance imaging.

Once the images are obtained, a reconstruction of bone, cartilage and soft tissues such as skin, mucosa, fatty tissue, among others, can be generated by segmenting each structure of the analyzed anatomy. The precise determination of each of these structures, as well as their thickness and shape, is essential in order to achieve a realistic and functional replica for training purposes. By using the information from diagnostic images and the segmentation process, it is possible to generate the complete three-dimensional digital model (200) of each of the structures of interest, which can be used during practice in the virtual simulator, as well as input to produce the model of the anatomical structure (101) that will be used during training.

In some embodiments of the invention, the model of an anatomical structure (101) can be produced by means of modeling or using 3D printing technology. The 3D printing technology used for this process can be selected from Fused Deposition Modeling (FDM), Polyjet, Electron-beam Freeform Fabrication (EBF3), Electron Beam Melting (EBM), Selective Heat Sintering (SHS), Selective Laser Sintering (SLS), projection binding (DSPC), Laminated Object Manufacturing (LOM), stereolithography (SLA), ultraviolet light photopolymerization (SGC) or a suitable combination of these techniques.

Figure 3:
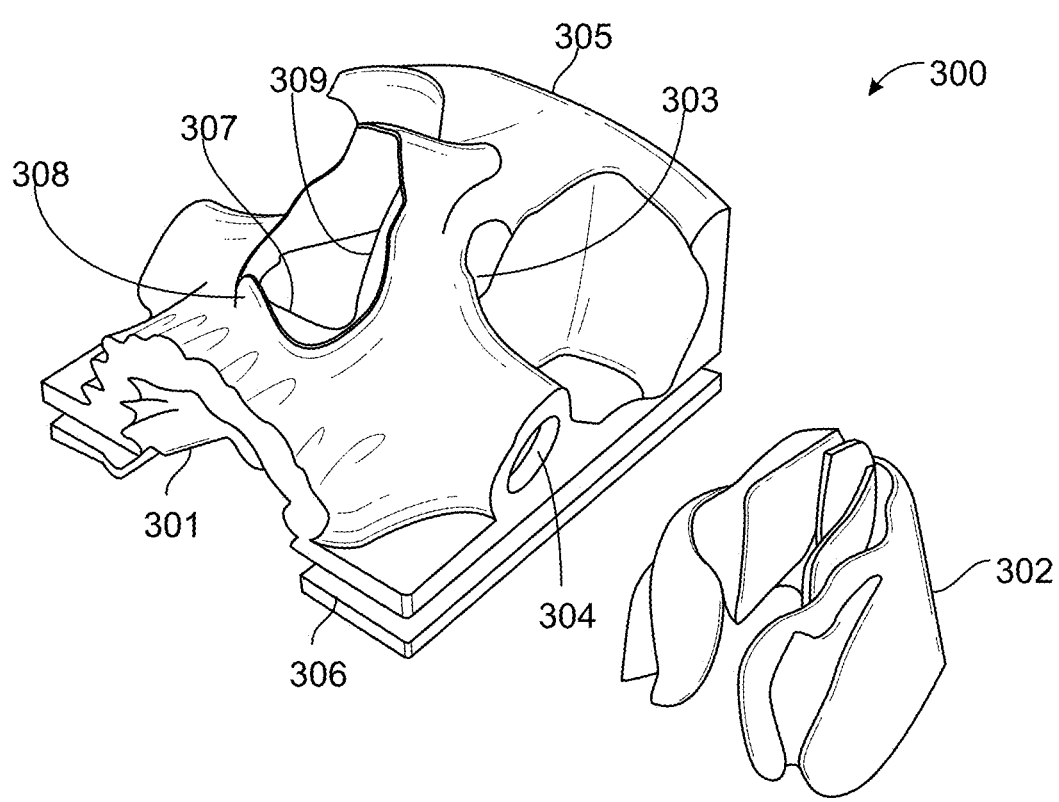
FIG. 3 corresponds to a maxilla and the turbinates of a bone structure produced in two parts of a model of the anatomical structure of the training station according to one embodiment of the invention.

As seen in FIG. 3, in preferred embodiments the model of the anatomical structure (101) comprises a bone structure (300), composed of the maxilla (301) and the turbinates (302). The bone structure (300) can be obtained by means of Selective Laser Sintering (SLS) using nylon or polystyrene, preferably nylon 11 or nylon 12. The modeling of the bone structure (300) by this method allows osteotomies to be performed with actual surgical instruments offering sensations similar to those of a real maxilla, since they are able to imitate the features of a real bone such as compression, tensile strength, flexion, elasticity, plasticity, rigidity, flexibility, resistance, among others. In particular embodiments of the invention, it is possible to combine the modeling material of the bone structure (300) with, for example, salts, which can give the material specific properties in the printed product, for example, piezoelectric properties, thereby enabling the use of the piezoelectric scalpel. Similarly, the bone structure (300) of the model of the anatomical structure (101) according to the present invention, preserves anatomical features of the maxilla such as the tear ducts (303), the maxillary sinuses (304), the frontal sinuses (305) among others.

In one embodiment of the invention, the bone structure (300) can be a single piece, or a combination of segments which will be added later to obtain the complete maxilla (301). The segmentation of the maxilla (301) allows for the development of interchangeable modules that facilitate introducing different features as, for example, additional changes to the endonasal or external anatomy. In particular, for the latter, a segment of the nasal bones could be made using a combination of special materials that would allow for the use of technologies such as the piezoelectric scalpel.

Furthermore, in preferred embodiments of the invention, the maxilla (301) comprises a channel (306) that surrounds the posterior edge of the maxilla (301), which allows the model to be fixed to the work base (900), positioning it in the most appropriate direction depending on working conditions.

Figure 4:
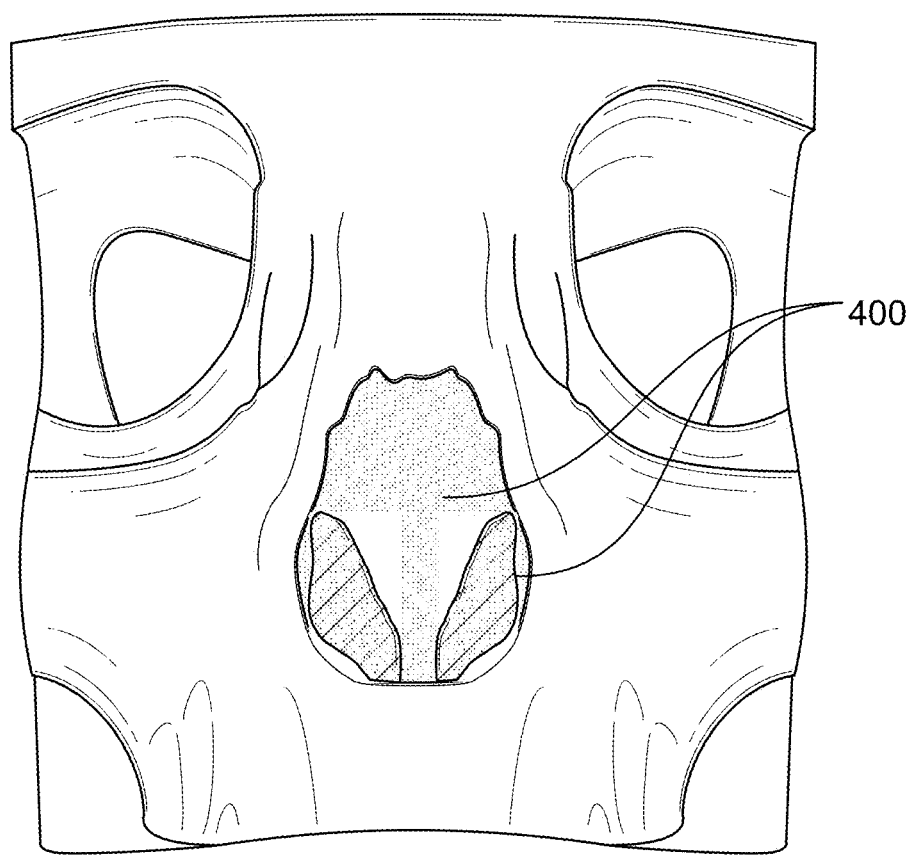
FIG. 4 shows the detail of a cartilaginous structure of a model of the anatomical structure of the training station according to an embodiment of the invention.

According to an embodiment of the invention as illustrated in FIG. 4, the cartilaginous structures (400) of the model of the anatomical structure (101) correspond to a faithful replica of a patient's anatomy, including desirable defects, such as deformities and deviations, maintaining their length, thickness, height and width. All of these particular features are determined and reproduced in accordance with the results of the segmentation and the three-dimensional digital model (200) as described above. The replicated cartilaginous structures (400) can be obtained by 3D printing using any one of the already mentioned technologies, with FDM or Polyjet being preferred in this case. In embodiments of the invention, thermoplastic filaments are used for FDM technology and pure thermoplastic filaments or composites for Polyjet technology. The aim of combining these materials is to obtain a Shore Hardness of between 50 and 90, thereby achieving sensations equivalent to those of real cartilage.

Manufacturing the soft tissues of the model of the anatomical structure (101) such as the skin, fatty tissue, muscle tissue and nasal mucosa according to the present invention, requires manufacturing the corresponding molds into which the corresponding material for each of the tissues will be injected. The molds can be manufactured by any of the 3D printing technologies mentioned above, with FDM being preferred, using PLA, ABS, ASA, PET, PETG, PC, PVA, TPU, or TPE filaments, being PLA filaments (polylactic acid) preferably used.

Figure 5:
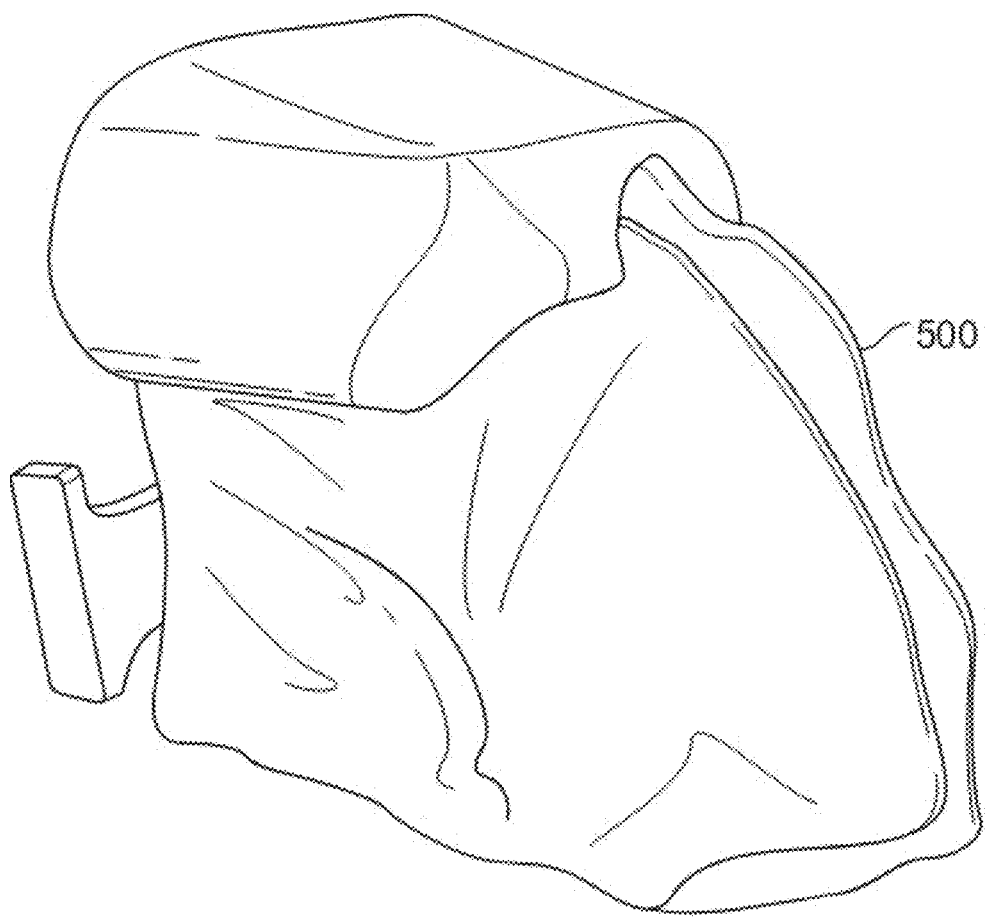
FIG. 5 corresponds to a mold that allows for the reproduction of the volume of air present inside the nose in a model of an anatomical structure of the training station according to an embodiment of the invention.

Preferably, in order to obtain a model of the anatomical structure (101) equivalent to the real structure, the volumes of air present inside these areas must be accurately replicated. In particular, as illustrated in FIG. 5, an element is used to replicate the accurate volume of air present inside the nose (500) in the nasal structure used as an example. The purpose of this volume of air is to fill the endonasal air space, leaving only a thin layer of silicone to reproduce the nasal mucosa, which surrounds the entire internal part of the nose. The features of the air volume mold allow for areas of greater or lesser thickness in the mucosa of the model as needed, thereby facilitating the patency of the nasal passages. The mold for the volume of air present inside the nose (500) can be obtained by means of any of the 3D printing technologies mentioned above, in this case FDM being preferred using TPU or TPE thermoplastic filaments, being TPU (thermoplastic polyurethane) filaments preferably used.

In some embodiments of the invention, the material selected to replicate the skin, fatty tissue and muscles, is one that allows for a faithful reproduction of the particular features of each of these tissues, such as elasticity, bendability, texture, hardness, and consistency, among others. In particular, the aim is to obtain Shore Hardness of between 20 and 90. Preferably, the selected material is a silicone rubber cured with peroxide or platinum, preferably a silicone cured with platinum, such as those known in the art as, for example, Equinox, SORTA-Clear, Smooth-Sil, Magikmold, Elkem, Bluestar, Mold Star, Dragon Skin, Rebound, Ecoflex, Body Double, Rubber Glass, Encapso-K. In some embodiments, if the selected silicone requires it, a vacuum degassing process is carried out which prevents the appearance of air bubbles and defects in the silicone when poured into molds.

Figure 6A:
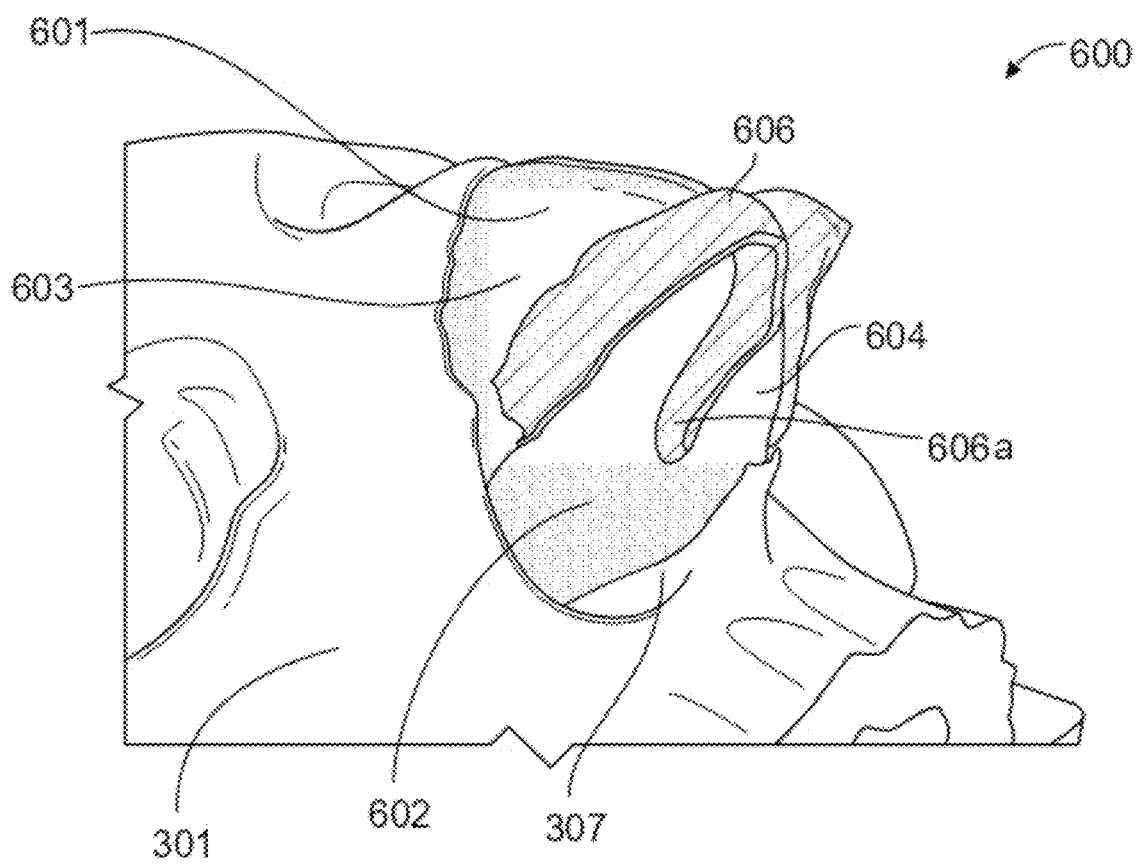
FIGS. 6a, 6b, 6c show an osteocartilaginous skeleton model of the anatomical structure of the training station according to an embodiment of the invention.

As seen in FIG. 6a, the osteocartilaginous skeleton (600) according to some embodiments of the present invention, is composed of the maxilla (301) and the nasal cartilaginous dorsum (601), the latter in turn composed of the nasal septum (602) and the upper lateral cartilages (603). The coupling of the maxilla (301) and the cartilage can be carried out by superimposing the structures, and fixing by means of a common adhesive, such as polyaddition, polymerization or polycondensation curing adhesives, preferably a polymerization curing adhesive, which secures the cartilage to the vomer (307) and the perpendicular plate of the maxilla (309).

Figure 6B:
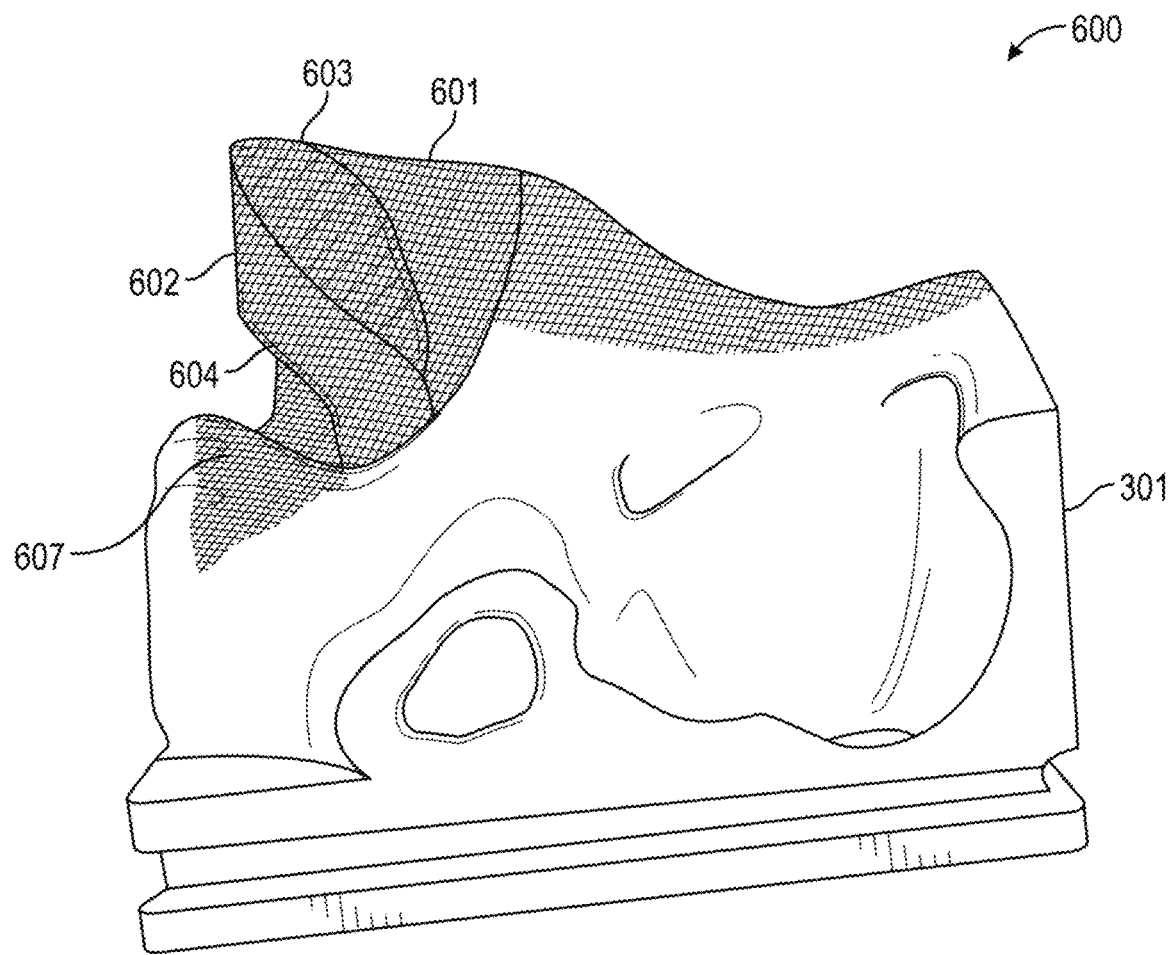
Figure 6C:
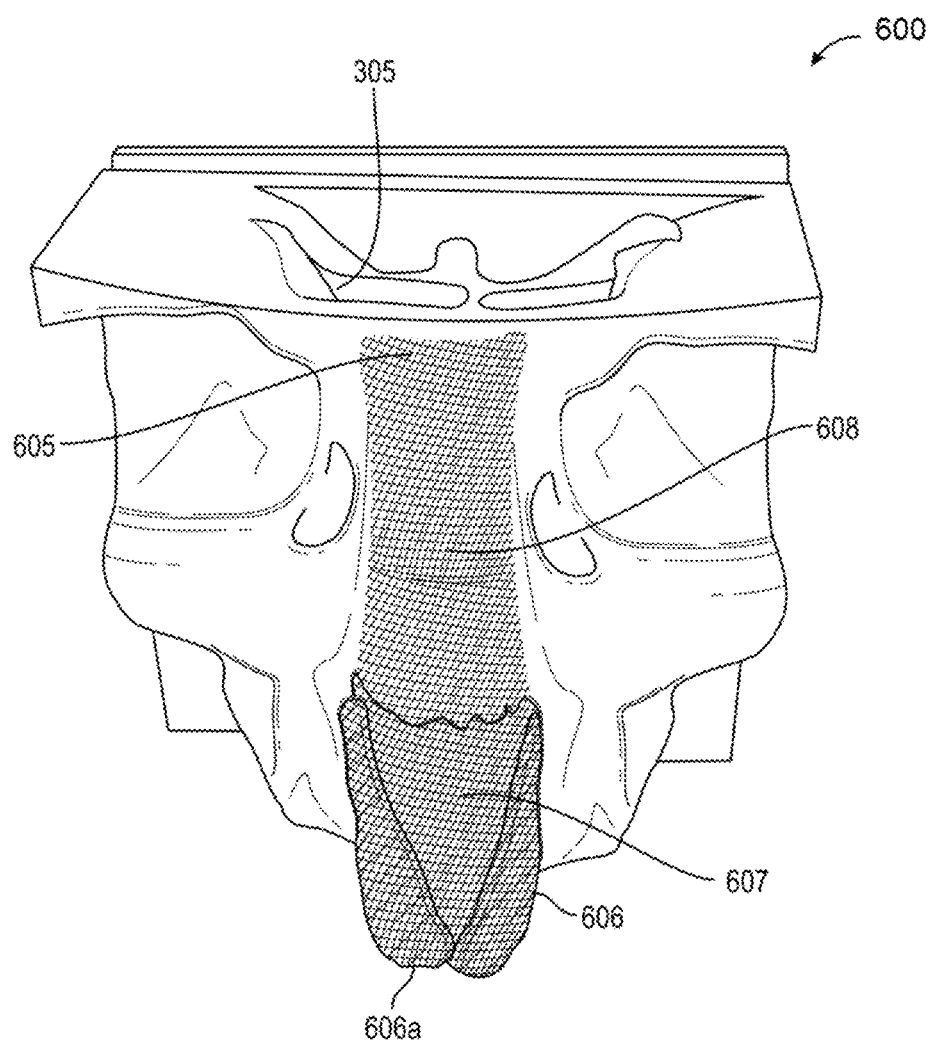

In some embodiments of the invention, as shown in FIGS. 6b and 6c, after setting the nasal septum (602), a nylon mesh (605) called rhinomesh can be included in the caudal and anterior part of the cartilage using a suitable adhesive, in this case a polyaddition curing adhesive being preferred. This mesh will later be integrated into the nasal mucosa that will cover the septal cartilage (602). In preferred embodiments of the invention, the mesh is placed from side to side covering an area corresponding to the first 30 mm to 5 mm of the anterior septum, as well as its caudal edge (604) and the nasal spine (308). The mesh simulates the adherence features of the mucoperichondrium and the so-called cross fibers found in a real nasal septum. Likewise, the mesh allows the user to be guided during septoplasty practice, by serving as a reference point to validate the correct dissection plane.

In order to guarantee a precise positioning of the lower lateral cartilages (606) that will make up the nasal tip of the model of the anatomical structure (101), a 3D printed mold can be used to facilitate the correct assembly of all the parts. In one embodiment of the invention, once all the elements of the osteocartilaginous skeleton (600) are in their final position, a new rhinomesh nylon mesh (605) can be placed over the elements of the nasal structure to simulate the perichondrium (for example, on the upper lateral cartilages (603) or on the lower lateral cartilages (606)) and the periosteum (608) (on the nasal bones and the ascending ramus of the maxilla). Additionally, the presence of the mesh allows for a clear reference point of the dissection plane that the user must follow when performing the surgery on the model of the anatomical structure (101), as well as a measurement means on which to mark the limits of the dissection plane of the dorsum at the level of the cartilages, which is usually supraperichondric (above the mesh), and subperiosteal (below the mesh) at the level of the nasal bones.

In preferred embodiments of the invention, given that decoupling of certain sections usually occurs, for example, in the lower lateral cartilages (606) of the model of the anatomical structure (101) of the nose, it is desirable to provide reinforcement to the feet of the lower crura (606a) in this area. Therefore, a nylon reinforcing mesh (607) can be included, which is inserted into the premaxilla (bone) and covers the lower part of the lower crura (606a) (cartilage), in turn enveloping the feet of the lower crura (606a). This mesh is adhered with a special adhesive, adding strength and reliability to the model.

According to some embodiments of the invention, the model of the anatomical structure (101) of the nose faithfully reproduces complex features of the anatomy such as the spaces in the external and internal nasal valve, as well as the thickness of the soft tissue that covers the nasal tip, the nasal dorsum, the nasal septum (602), the turbinates (302), the muscle tissue that covers the external structure of the nose and maxilla (301), among others. All of the above while maintaining the patency of the simulated nostrils. Therefore, including soft tissues on the osteocartilaginous skeleton (600) may involve the manufacture and use of 3D molds that allow reproducing these features precisely.

Figure 7A:
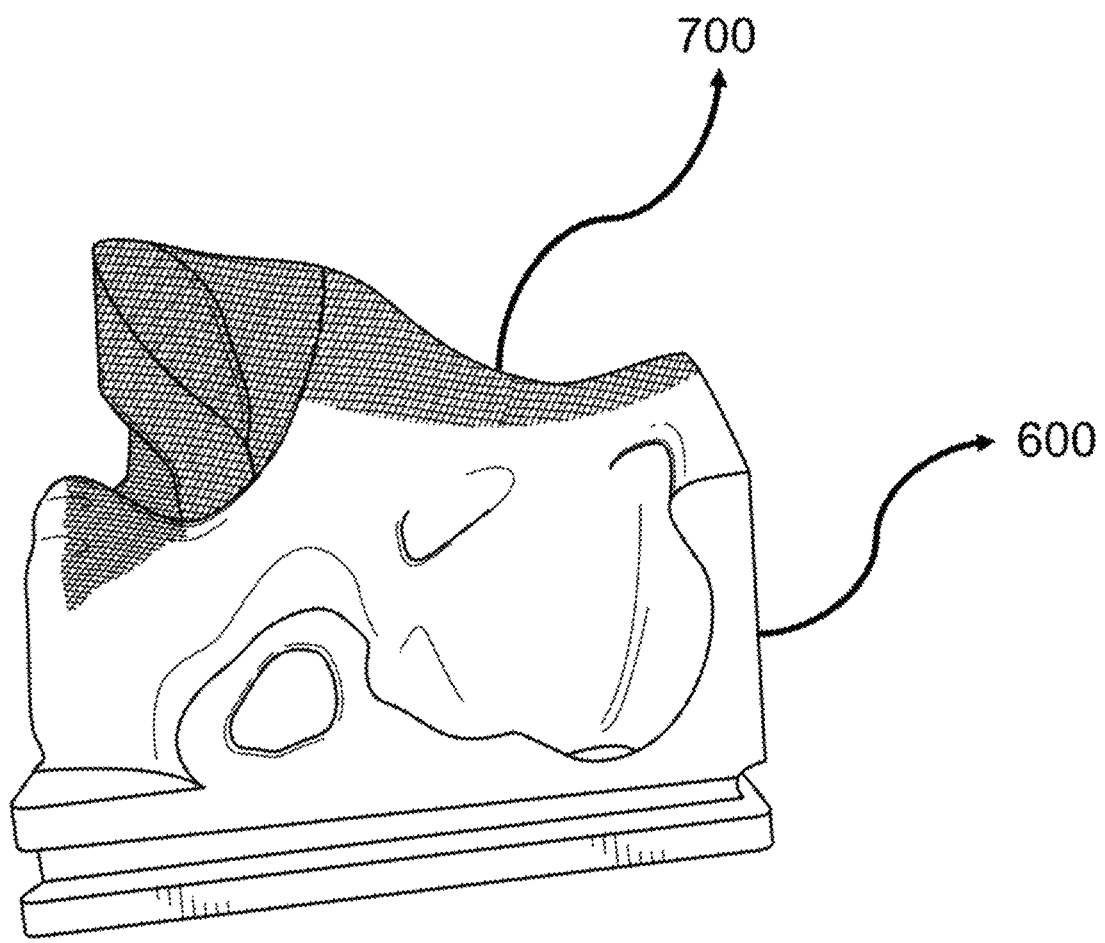
FIGS. 7a and 7b show a layer of soft tissues covering an osteocartilaginous skeleton and the nasal mucosa in the inner part of the nose of a model of the anatomical structure of the training station according to an embodiment of the invention.
Figure 7B:
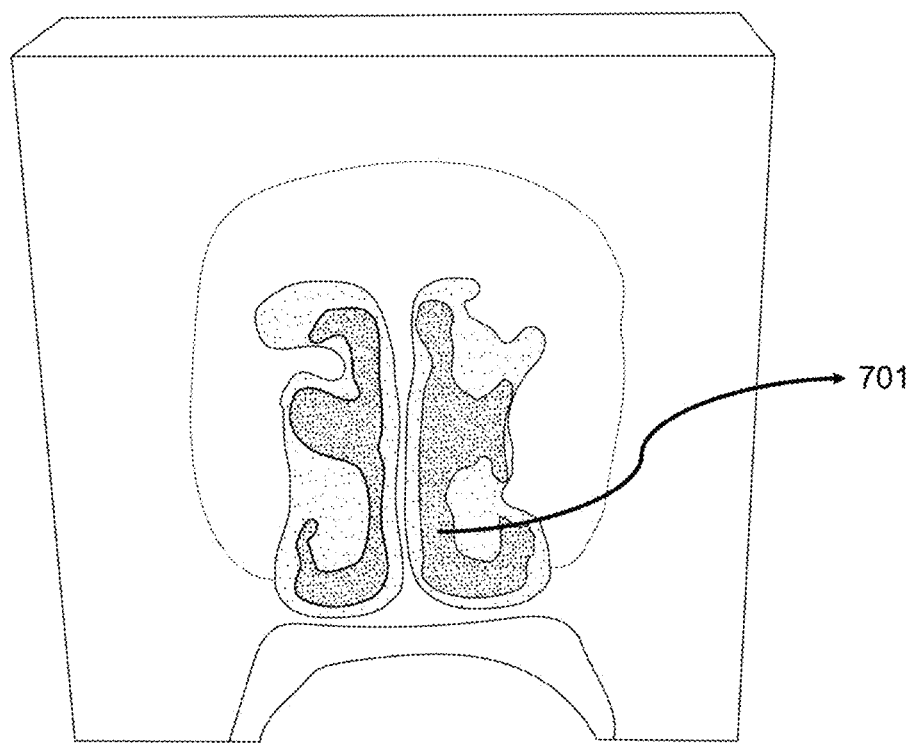

According to the above, as seen in FIGS. 7a and 7b, in the example of the model of the anatomical structure (101) of the nose, the silicone of the muscle layer (700) is firmly coupled to the osteocartilaginous skeleton (600), penetrating between the cartilaginous structures (400), which allows recreating the adherence that simulates in great detail the ligaments of the nose (Pitanguy's midline, scroll and interdomal ligaments) allowing for a better understanding of the anatomy of the nasal tip and the nasal cartilaginous dorsum (601). A precise anatomy is obtained having the soft tissues attached using this method, which also offers dissection sensations in the tissues comparable to the real sensations in terms of consistency, texture, flexibility, among others. To achieve a precise coupling of the muscle layer (700) on to the osteocartilaginous skeleton (600), it is possible to arrange the osteocartilaginous skeleton (600) within a 3D printed mold, into which the selected degassed silicone will be poured to create the mucous membranes (701) and the muscle (700). The empty spaces between the mold and the osteocartilaginous skeleton (600) will thereby be covered in silicone, acquiring the shape and thickness of the desired structures.

Figure 8A:
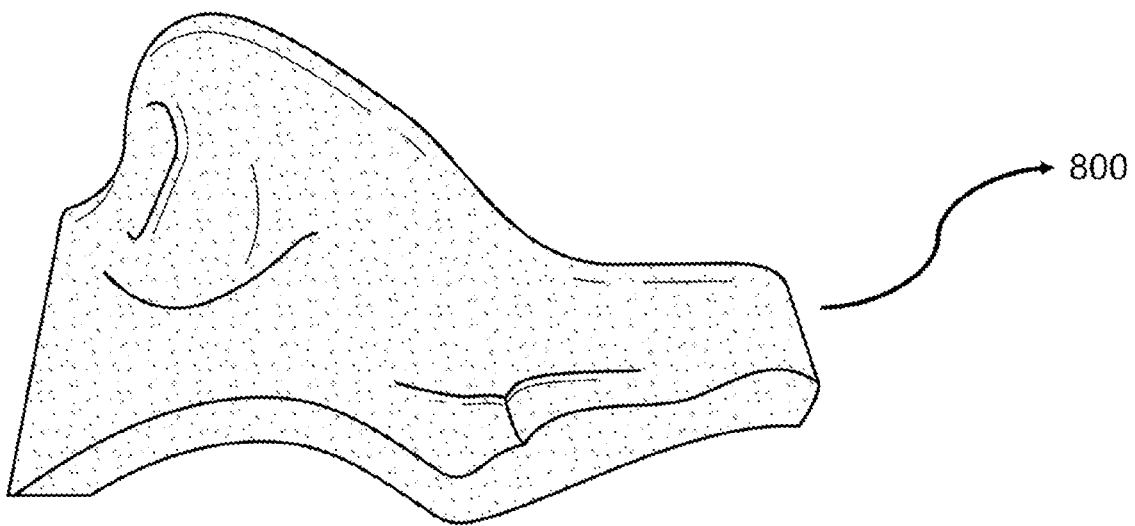
FIGS. 8a and 8b show a skin layer, as well as the reinforcing mesh on the inside surface thereof of the anatomical structure of the training station according to an embodiment of the invention.

As for the manufacturing of the nasal mucosa (701) and the muscle (700), the skin layer (800) shown in FIG. 8a, and the subcutaneous fatty tissue of the model of the anatomical structure (101) of the nose according to the exemplary embodiment of the present invention, these require manufacturing specifically designed 3D molds using the segmentation information and the processing of the images obtained from the reference patient, designed to maintain the patency of the nares and facilitate adhesion to the alar cartilages of the osteocartilaginous skeleton (600). The selected material seeks to simulate the features of elasticity, hardness and flexibility of human skin. In preferred embodiments of the invention, once the skin layer (800) is obtained, the fatty tissue is added in specific areas of the inside surface of the skin (800), which is reproduced using a silicone with features and color similar to human fat.

Figure 8B:
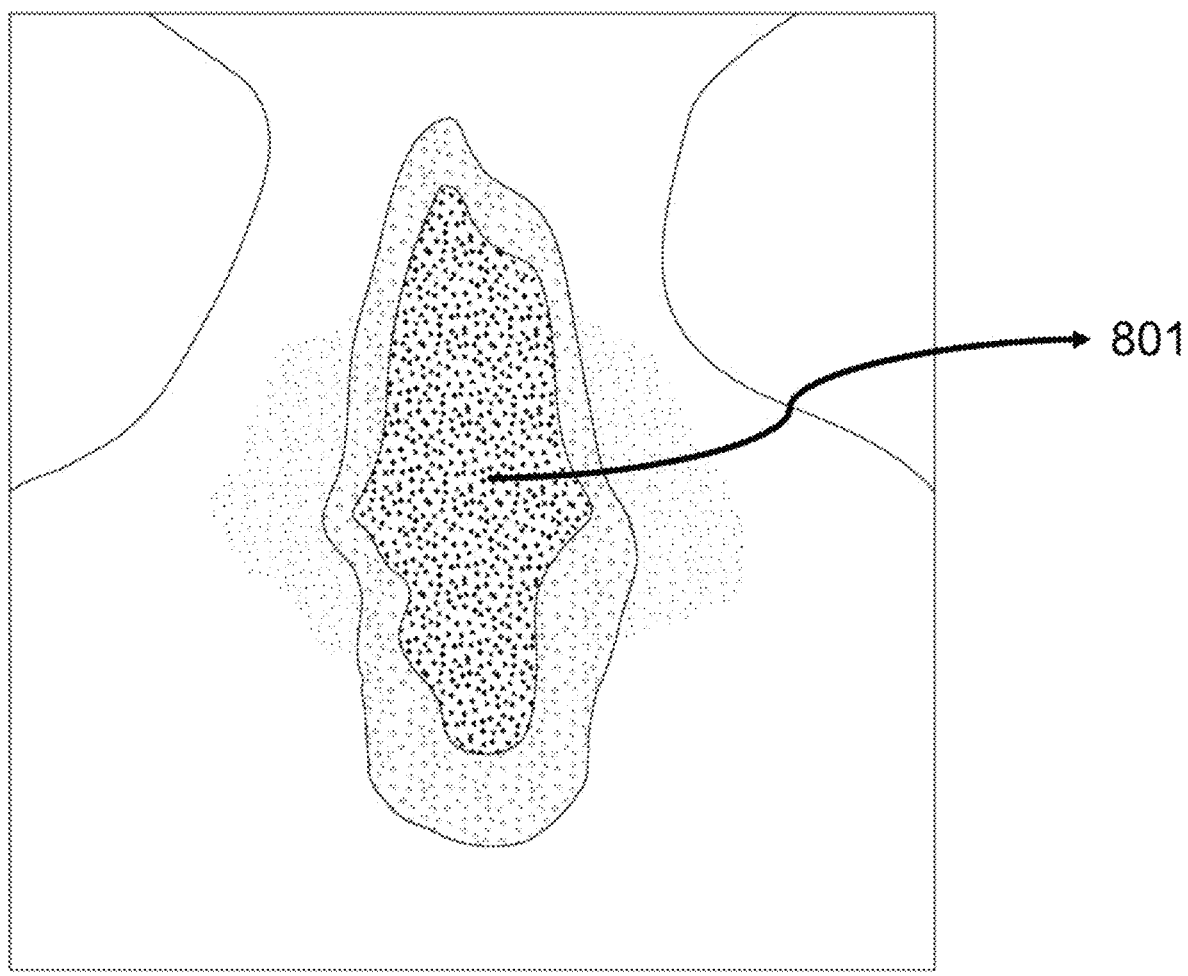

In order to reinforce the skin (800) in the areas of greatest tensile strength, in preferred embodiments as illustrated in FIG. 8b, a nylon mesh (801) is integrated into the skin along the dorsum, the tip and the columella through a fusion process, which consists of fixing the nylon mesh to the inside surface of the skin (800). Once the nylon mesh (801) is placed in the desired position, a layer of silicone is applied and the assembly of skin (800) and nylon mesh (801) is introduced into a specially designed 3D mold, which by means of pressure from its parts, fuses the nylon mesh (801) to the inside surface of the skin (800), generating an optimal adhesion between both elements.

According to some particular embodiments of the invention, the layer of skin (800) together with all its particular features can be coupled to the osteocartilaginous structure together with the already finished muscle layer (700) by means of methods known in the art, such as fusion, or by pouring silicone onto the osteocartilaginous structure and the muscle layer; being the fusion method preferred in this case. In preferred embodiments this process is mediated by a specially designed mounting mold that uses silicone to adhere the skin (800) to the underlying structure. Once the silicone drying process is finished, the fusion of all the layers and elements that make up the model is completed.

Figure 9A:
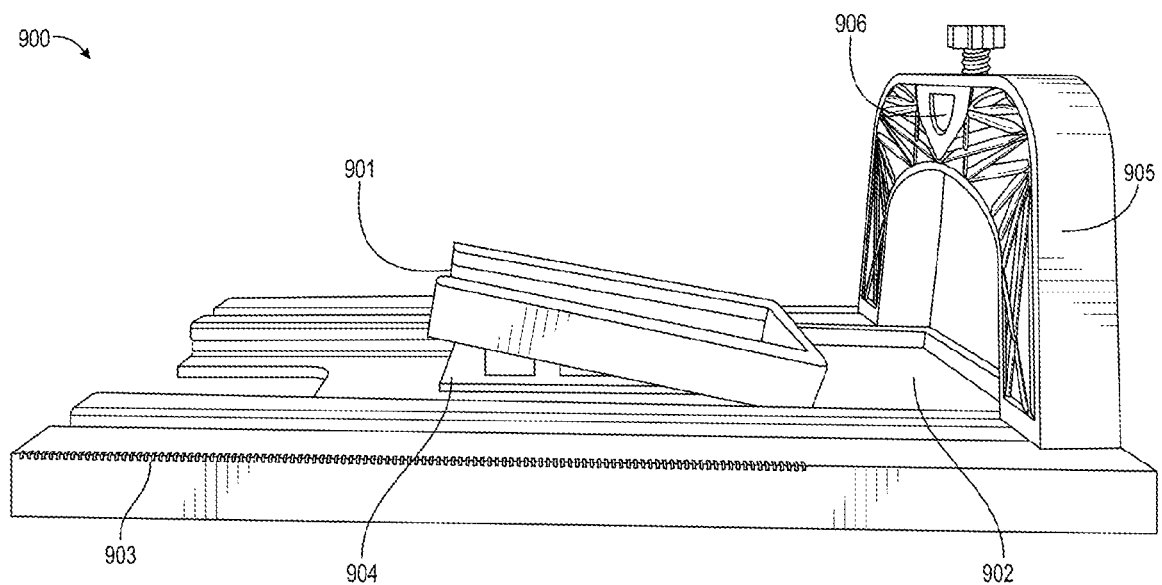
FIGS. 9a, 9b and 9c correspond to a work base of the training station according to an embodiment of the invention.
Figure 9B:
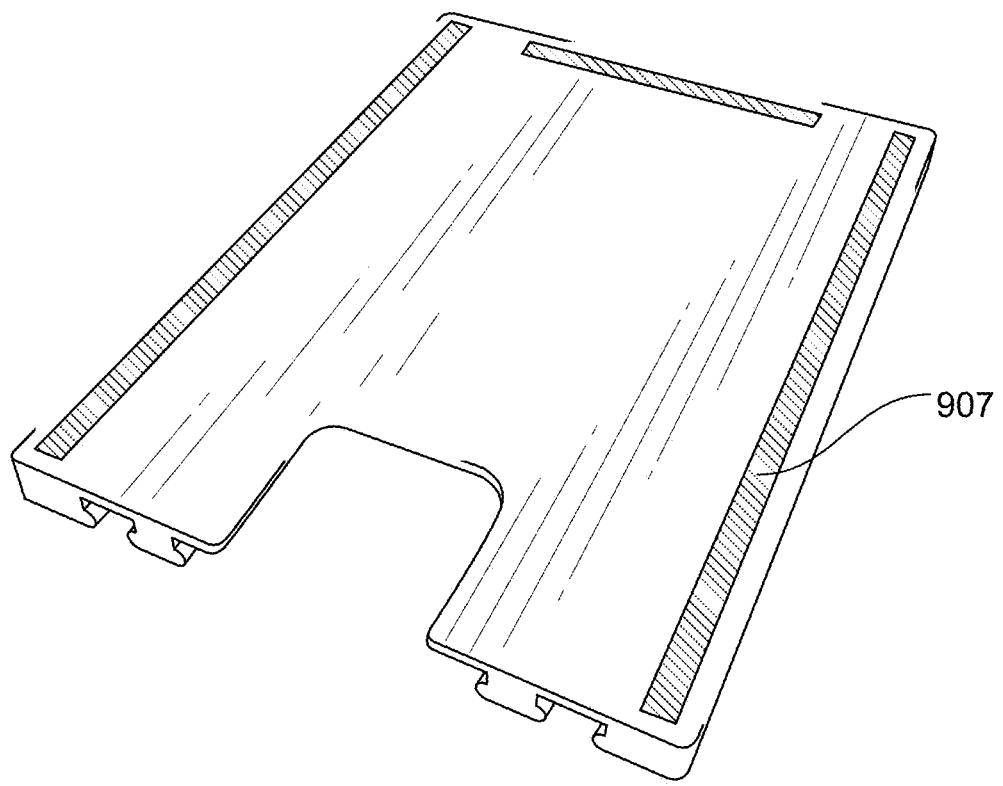
Figure 9C:
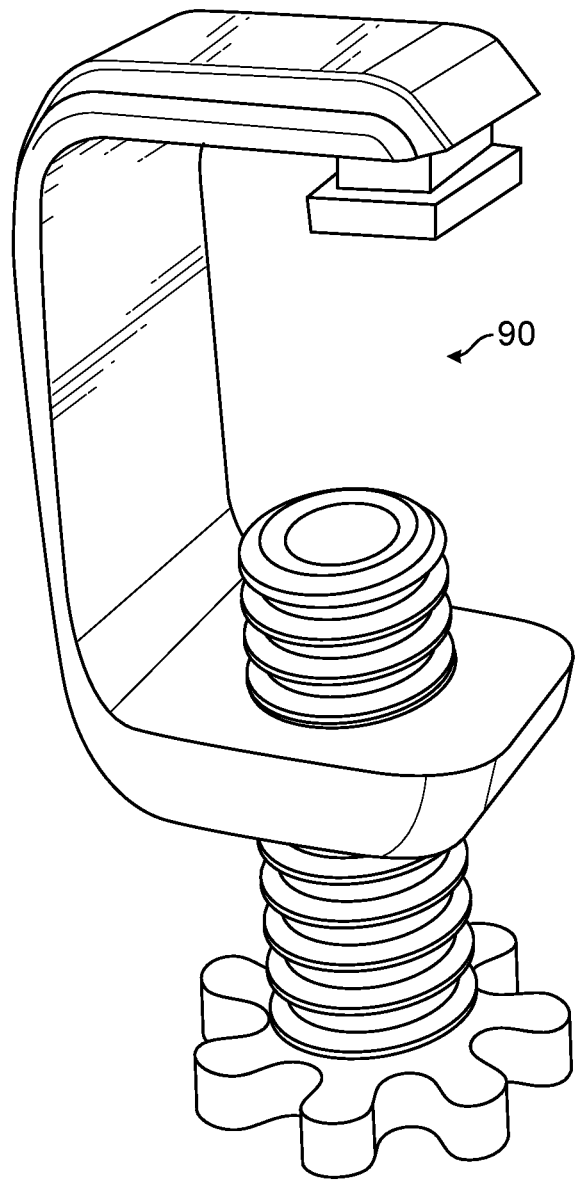

In embodiments of the invention illustrated in FIGS. 9a to 9c, the model of the anatomical structure (101) is also accompanied by a work base (900), by means of which it is possible to attach the model of the anatomical structure (101), fixing it to a stable surface such as a table or the like. In order to obtain a proper fit, the channels (306) of the maxilla (301) fit into a rail coupling (901), and it in turn into the central part of the mounting base (902). In some embodiments of the invention, the rail coupling (901) can be oriented in any direction, so that the model can be adapted for right- or left-handed users, or depending on the conditions of the space in which the training is performed. Additionally, in particular embodiments of the invention, the mounting base (902) has millimeter rulers (903) incorporated onto the sides allowing the user to measure different elements during training. In some embodiments of the invention, the rail coupling (901) also includes a multifunction wedge (904), which allows the inclination to be changed about an anteroposterior or lateral axis according to user needs.

In some embodiments of the invention, the mounting base (902) also includes a fixing system that comprises a series of non-slip silicone bands (907) on the edges of the rear area of the mounting base (902), along with a clamp system (908) that can be placed on one or both side rails of the mounting base (902), allowing the model to be firmly fixed to the table or underlying surface.

Additionally, in particular embodiments of the invention, the work base (900) also provides a bridge (905) that includes a mounting system for instruments (906), which during most of the training phases enables optimal exposure of the anatomy of the model, and also allows the users to have their hands free during most of the training.

The manufacturing methods of the elements of the work base (900) are not particularly limited, so they can be obtained either by means of any of the 3D printing methods mentioned above or by manual modeling.

The invention claimed is:

1. A training station for surgical procedures comprising:
    a model of an anatomical structure,
    a three-dimensional digital model of the model of an anatomical structure, and
    a work base,
    where the model of an anatomical structure corresponds to an equivalent anatomical conformation of a patient and is made up of materials that simulate bones, cartilage and skin;
    wherein the three-dimensional digital model of the model of an anatomical structure allows a training station user to interact with a representation of the model of an anatomical structure through augmented reality systems and/or virtual reality; and
    where the work base has a clamp system for fixing the work base to the surface on which the training is carried out, and also has an adjustable multifunction wedge for modifying an angle of the model during training;
    wherein the model of an anatomical structure comprises a bone structure, a cartilaginous structure and a soft tissue structure;
    wherein the model of an anatomical structure comprises a soft tissue structure which includes nasal mucosa, muscle, fat and skin;
    wherein the model of an anatomical structure comprises nylon meshes located between the material that simulates cartilage and the material that simulates muscle;

wherein the nylon mesh is included in the caudal and anterior part of the cartilage using a polyaddition curing adhesive;

wherein the nylon mesh is integrated into the nasal mucosa that covers the septal cartilage.

2. The training station according to claim 1, wherein the model of an anatomical structure is obtained from diagnostic images from computed tomography.

3. The training station according to claim 1, wherein the model of an anatomical structure comprises a soft tissue structure which is composed of silicone rubbers.

4. The training station according to claim 1, wherein the model of an anatomical structure is of a head or neck structure selected from the group comprising pinna, temporal bone, lower or upper maxilla, or nasal structure.

5. The training station according to claim 1, wherein the model of an anatomical structure is a nasal model.

6. The training station according to claim 1, wherein the work base comprises a rail coupling, a mounting base and a clamp system.

7. The training station according to claim 1, wherein the work base includes a rail coupling which comprises a multifunction wedge to change an inclination about an axis of the rail coupling.

8. The training station according to claim 1, wherein the work base further comprises a bridge that includes a mounting system for instruments.

* * * * *